United States Patent [19]

Dorlars et al.

[11] 4,005,098

[45] Jan. 25, 1977

[54] TRIAZOLYL-COUMARINS

[75] Inventors: Alfons Dorlars, Leverkusen; Carl-Wolfgang Schellhammer, Opladen; Wolf-Dieter Wirth, Cologne-Stammheim, all of Germany

[73] Assignee: Bayer Aktiengesellschaft, Leverkusen, Germany

[22] Filed: Mar. 12, 1969

[21] Appl. No.: 806,732

[30] Foreign Application Priority Data

Mar. 16, 1968 Germany .................... 1670999

[52] U.S. Cl. .................. 260/308 A; 252/301.29; 260/249.5; 260/249.6; 260/249.8; 260/308 B
[51] Int. Cl.² .................................. C07D 405/14
[58] Field of Search ........ 260/308 A, 308 R, 308 B

[56] References Cited

UNITED STATES PATENTS 3,496,188  2/1970  Wirth ............................... 260/308

Primary Examiner—Alton D. Rollins
Attorney, Agent, or Firm—Plumley and Tyner

[57] ABSTRACT

Triazolyl-coumarins of the formula

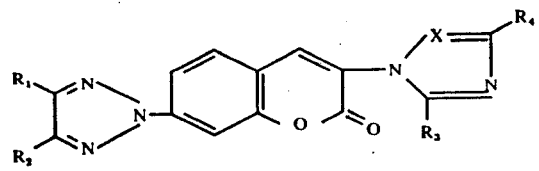

wherein $R_1$ to $R_4$ and X are as defined herein, or their quaternization products are useful as brightening agents.

8 Claims, No Drawings

TRIAZOLYL-COUMARINS

The object of the present invention comprises 7-[v-triazolyl-(2)]-3-[imidazolyl-(1)- and as-triazolyl-(1)]-coumarins of the general formula

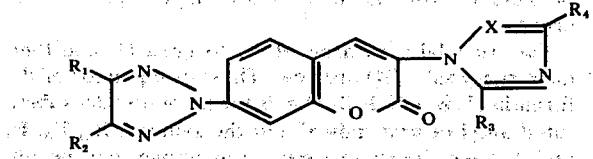

(I)

in which $R_1$ denotes hydrogen or an optionally substituted alkyl or aryl radical; $R_2$ means hydrogen, an optionally substituted alkyl or aryl radical, cyanogen, the carboxyl group, a carboxylic acid ester group, an optionally substituted carboxylic acid amide group or an acylated amino group; $R_1$ and $R_2$ together with the two carbon atoms of the triazole ring may form a 5- or 6-membered nonaromatic ring system; $R_3$ and $R_4$, independently of one another, stand for hydrogen or an optionally substituted alkyl or aryl radical; the ring member X stands for a nitrogen atom or the group $C-R_5$ where $R_5$ may denote hydrogen or an alkyl radical, or their quaternisation products of the general formula

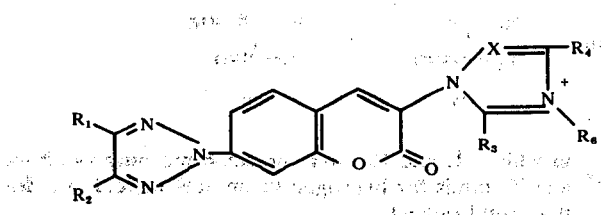

(II)

in which $R_1$ to $R_5$ and X have the same meaning as above; $R_6$ stands for an optionally substituted alkyl radical; Y denotes an anion; and the coumarin ring may contain further substituents,
as well as the production of these compounds and their use as brightening agents.

The optionally substituted alkyl radical which may be represented by $R_1 - R_6$ comprise straight-chain, branched or cyclic, saturated or unsaturated alkyl groups with 1 – 12 carbon atoms, which may be substituted by substituents such as halogen atoms, for example fluorine, chlorine and bromine; hydroxyl groups; alkoxy groups with 1 – 4 carbon atoms; alkyl-carbonyloxy groups with 1 – 4 carbon atoms in the alkyl radical; carboxylic acid groups; alkoxy-carbonyl groups with 1 – 4 carbon atoms in the alkyl group; or phenyl radicals which may carry halogen atoms, lower alkyl and alkoxy groups.

Suitable alkyl radicals are, for example: methyl, ethyl, β-hydroxyethyl, β-acetoxyethyl, β-chloroethyl, carboxyethyl, carbethoxyethyl, ethoxyethyl, n- and iso-propyl, n-, iso- and tert.-butyl, iso-butenyl, pentyl, hexyl, octyl, decyl, dodecyl, benzyl, p-chlorobenzyl and β-phenylethyl radicals.

The optionally substituted aryl radicals primarily comprise phenyl radicals which may carry one or more substituents, for example, fluorine, chlorine, bromine, cyanogen, lower alkyl and alkoxy groups with 1 – 4 carbon atoms (which may, in turn be further substituted, for example, by phenyl radicals or the carboxyl group), alkoxy-carbonyl groups with 1 – 5 carbon atoms, alkyl-sulphonyl groups with 1 – 4 carbon atoms, phenyl and phenoxy radicals.

Examples of such radicals are the following: phenyl, o-, m- and p-fluorophenyl, o-, m- and p-chlorophenyl, o-, m- and p-bromophenyl, o-, m- and p-tolyl, o-, m- and p-anisyl, m- and p-cyanophenyl, m- and p-ethoxycarbonylphenyl, m- and p-methane-sulphonylphenyl, m- and p-ethanesulphonylphenyl, p-benzylphenyl, p-benzyloxyphenyl, p-phenoxyphenyl radicals, p-biphenylyl radicals.

Non-aromatic ring systems which are anellated to the v-triazole ring and may be represented by $R_1$ and $R_2$ together with the two carbon atoms of the v-triazolering, are primarily cyclopentane and cyclohexane rings which may, in turn, be anellated to a benzene ring. Examples of these anellated systems are the following:

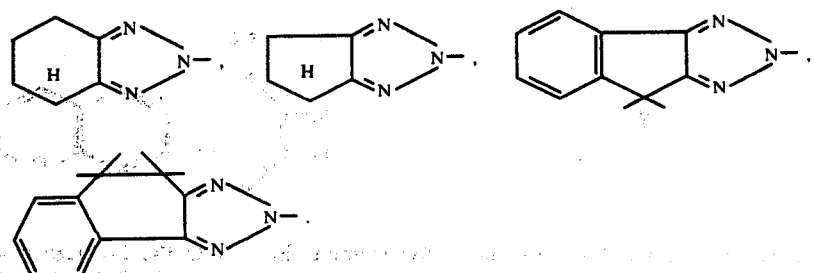

Suitable carboxylic acid ester groups $R_2$ are, for example, alkoxy-carbonyl groups with 1 – 4 carbon atoms in the alkoxy group, such as methoxy-carbonyl, ethoxy-carbonyl or butoxy-carbonyl radicals.

An optionally substituted carboxylic acid amide group is, for example, a carboxylic acid amide group which is mono- or disubstituted by alkyl radicals with 1

– 4 carbon atoms. Examples are the groups -CONH$_2$, -CONHCH$_3$, -CONHC$_4$H$_9$, -CON(CH$_3$)$_2$ and -CON(C$_4$H$_9$)$_2$.

Suitable acylamino groups R$_2$ are, for example, amino groups which are linked to one of the following acyl radicals:

alkoxycarbonyl groups with 1 – 4 carbon atoms in the alkoxy group; alkyl-carbonyl groups with 1 – 10 carbon atoms in the alkyl radical; alkenyl-carbonyl groups with 1 – 10 carbon atoms in the alkenyl radical; aryl-carbonyl groups, in particular optionally substituted phenylcarbonyl groups; and triazinyl groups which may be further substituted by halogen, alkoxy, aryloxy, amino, alkylamino, dialkylamino, arylamino, alkylarylamino, alkyl or aryl radicals.

A suitable acylated amino group is, furthermore, the N-pyrrolidonyl radical.

Examples of the acyl radicals mentioned above are: acetyl, chloroacetyl, ethoxyacetyl, phenylacetyl, propionyl and acryl or methacryl radicals; butyryl, isobutyryl, valeryl, pivaloyl, benzoyl, toluyl, chlorobenzoyl, anisoyl, 4-chloro-6-methoxy-s-triazinyl-(2), 4-chloro-6-ethoxy- and -propoxy-s-triazinyl-(2), 4,6-bis-dimethylamino, diethylamino and -dipropyl-amino-s-triazinyl-(2), 4-methyl-6-methoxy- and -ethoxy-s-triazinyl-(2), and 4,6-dimethoxy- and -diisopropoxy-s-triazinyl-(2) radicals.

Suitable alkyl substituents R$_3$, R$_4$ and R$_5$ are primarily those with 1 – 4 carbon atoms. The anion Y is preferably a colourless anion which either originates from the quaternising agent used or is introduced by exchange of the anion originally present. Examples are: Cl, Br, sulphonate groups such as CH$_3$O-SO$_3$, benzene sulphonate, toluene sulphonate, phosphate, acetate, chlorozincate, perchlorate, nitrate, sulphate and oxalate radicals.

The compounds of the general formula (II) are obtained by reacting compounds of the formula (I) with quaternising agents in known manner, for example, in an inert organic solution. Suitable alkylating agents are, for example, the esters of strong mineral acids and organic sulphonic acids with, preferably, low-molecular alcohols, such as alkyl chlorides, alkyl bromides, aralkyl halides, dialkyl sulphates, and esters of sulphonic acids of the benzene series, such as the methyl, ethyl, propyl, n-butyl esters of benzene-sulphonic acid, p-methylbenzene-sulphonic acid, p-chlorobenzene-sulphonic acid and p-nitrobenzene sulphonic acid.

Suitable inert organic solvents are, for example, highboiling aliphatic, cycloaliphatic or aromatic hydrocarbons, or stable aliphatic or cyclic halogen compounds, such as carbon tetrachloride, tetrachloroethylene, mono- or dichlorobenzene, and also nitrobenzene. If the reaction conditions are not too energetic, it is also possible to work in an excess of liquid quaternising agent.

The triazolyl-coumarins of the formula (I) and their quaternary salts (II) are new. Those compounds of the formula (I) in which R$_2$ stands for an optionally substituted alkyl or aryl radical and the symbols R$_1$, R$_3$, R$_4$ and X have the same meaning as above, can be obtained, for example, by condensing 7-hydrazinocoumarin derivatives of the formula

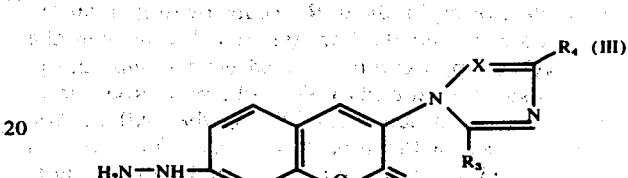

in which R$_3$, R$_4$ and X have the same meaning as above and the coumarin ring may contain further substituents, with α-oximino-ketones of the formulae

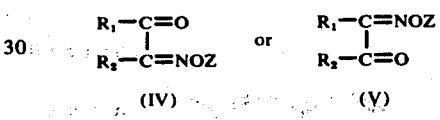

in which R$_1$ and R$_2$ have the same meaning as above and Z stands for hydrogen or an acyl radical, e.g. for the acetyl radical, and converting the resultant α-oximino-hydrazones of the formulae

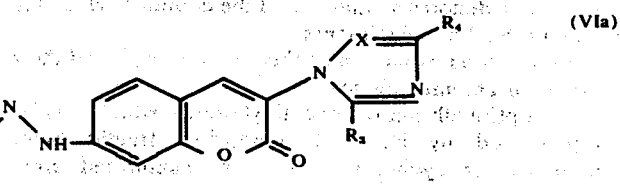

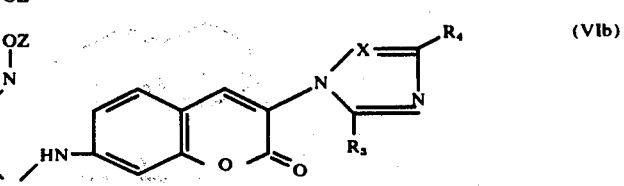

into the 7-v-triazolyl-(2)-coumarin compounds of the formula (I) in which R$_2$ has the same meaning as above, with the elimination of HOZ, and, if desired, subsequently converting the substituents R$_1$ or R$_2$ in known manner.

The elimination of HOZ is carried out, for example, by simple heating with dehydrating agents, such as acetic anhydride, possibly in the presence of sodium acetate or pyridine bases; or carbodiimides such as dicyclohexyl carbodiimide, at elevated temperatures, for example 60° – 130° C; it is also possible to work in mixtures of acetic anhydride and strongly polar solvents such as dimethyl formamide, diethyl formamide or N-methyl pyrrolidone.

The hydrazino-coumarin derivatives of the formula (III) can be prepared in known manner by condensing 4-acetamino-2-hydroxy-benzaldehyde or its anile with 1,2,4-triazolyl-(1)-acetic acids or imidazolyl-(1)-acetic acids of the formula

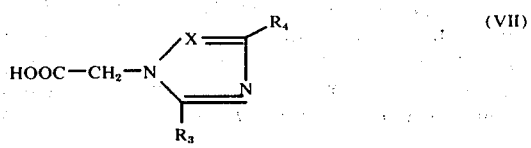

(VII)

in which $R_3$, $R_4$ and X have the same meaning as above, to form 7-acetamino-3-[1,2,4-triazolyl-(1)- or -imidazolyl-(1)]-coumarins, subsequently hydrolysing the acetamino group to form the amino group, diazotising the latter, and reducing the resultant diazonium group in a suitable manner to form the hydrazino group. Suitable triazolyl- or imidazolyl-acetic acids (VII) are, for example: 1,2,4-triazolyl-(1)-acetic acid, 3,5-dimethyl-1,2,4-triazolyl-(1)-acetic acid, 3-phenyl-1,2,4-triazolyl-(1)-acetic acid, imidazolyl-(1)-acetic acid, 2-methyl-imidazolyl-(1)-acetic acid, 4,5-dimethyl-imidazolyl-(1)-acetic acid, 3-phenylimidazolyl-(1)-acetic acid.

Suitable compounds (IV) or (V) are, inter alia: oximino-acetone, diacetyl monoxime, 1-oximino-butanone-(2), 1-phenyl-2-oximino-butanone-(3), 1,3-diphenyl-1-oximinopropanone-(2), oximinobenzyl-cyclohexylketone, 1-oximino-4-phenyl-butene-(3)-one-(2), 2-oximino-pentanone-(3), 3-oximino-4-methyl-pentanone-(2), 1-oximino-4-methyl-penten-(3)-one-(2), 3-oximino-pentanol(5)-one-(2), 3-oximino-hexanone-(2), 2-oximino-5-methyl-hexanone-(3)-2-oximino-heptanone-(3), 3-oximino-heptanone-(4), 3-oximino-octanone-(2), 4-oximinononanone-(5), 3-oximino-tridecanone-(2), 2-oximino-cyclohexanone-(1), oximino-acetophenone, p-fluoro, p-chloro-, p-bromo-, p-methyl- and p-methoxy-oximino-acetophenone, oximino-propiophenone, p-fluoro-, p-chloro-, p-bromo-, p-methyl-, p-benzyl-, p-methoxy- and p-benzyloxy-oximino-propiophenone, p-dimethylbenzyl-oximinopropiophenone, p-ethyl- and p-tert.-butyl-oximinopropiophenone, 1-oximino-1-phenylacetone, 1-oximino-1-o-, -m-, and -p-tolylacetone, 1-oximino-1-o-, -m- and -p-anisylacetone, 1-oximino-1-o-, -m- and -p-chlorophenylacetone, 1-oximino-1-m- and -p-cyanophenylacetone, 1-oximino-1-m- and -p-carbethoxy-phenylacetone, 1-oximino-1-m- and -p-methanesulphonyl-phenylacetone, oximino-butyrophenone, γ-benzoyl-γ-oximino-butyric acid methyl and ethyl ester, 2-oximino-1,3-diphenylpropanone-(1), benzilmonoxime, oximino-cyclopentanone, oximino-cyclohexanone, 2-oximino-indanone-(1), 2-oximino-tetralone-(1), p-phenyloximino-propiophenone, p-phenoxy-oximinopropiophenone.

Triazolyl-coumarins of the formula (I) in which $R_2$ stands for cyanogen, the carboxyl group, a carboxylic acid ester group or an optionally substituted carboxylic acid amide group, and the symbols $R_1$, $R_3$, $R_4$ and X have the same meaning as above, can be obtained, for example, by diazotising 7-amino-coumarin derivatives of the formula

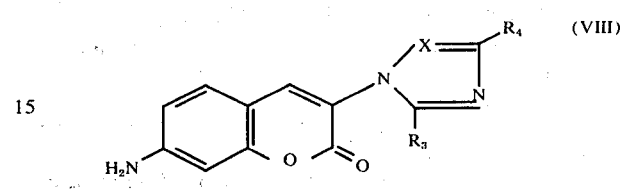

(VIII)

in which $R_3$, $R_4$ and X have the same meaning as above and the coumarin ring may contain further substituents; coupling with enamines of the formula

(IX)

in which $R_1$ and $R_2$ have the same meaning as above, for example, with p-aminocrotonic acid nitrile, esters or amides, or with p-aminocinnamic acid nitrile, esters or amides; converting the resultant azo compounds of the formula

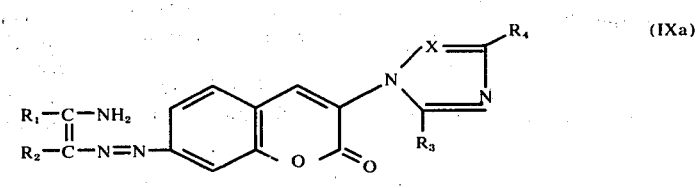

(IXa)

in which $R_1$ - $R_4$ and X have the same meaning as above, with the aid of copper(II) salts into the copper complexes; converting the latter by oxidation, for example, by heating in the presence of an excess of a solution of a complex copper(II) salt, into the 7-v-triazolyl-(2)-coumarin compounds; and, if desired, hydrolysing the carboxylic acid nitrile, ester or amide group to form the carboxyl group.

Those triazolyl-(2)-coumarins of the formula (I) in which $R_2$ stands for an acylated amino group and $R_1$, $R_3$, $R_4$ and X have the same meaning as above, can be prepared, for example, by coupling the diazo compounds obtainable by diazotisation of 7-amino-coumarin compounds of the formula (VIII), with -nitro-oximes of the formula

(X)

in which $R_1$ has the same meaning as above, for example, with nitroacetaldoxime or with ω-nitroacetophenone-oxime, cyclising the resultant azo compounds to form the corresponding 7-(4-nitrotriazolyl-(2)-coumarin derivatives, reducing these to form the amino compounds of the formula

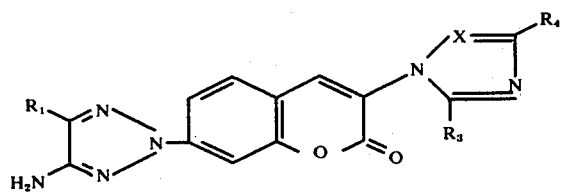

(Xa)

and converting these into the acylamino compounds.

Triazolyl-coumarins of the formula (I) in which $R_2$ stands for an acylated amino group and $R_1$, $R_3$, $R_4$ and X have the same meaning as above, can also be obtained by condensing 7-hydrazino-coumarin compounds of the formula (III) with 1,2,4-oxodiazoles of the formula

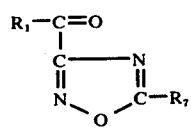

(XI)

in which $R_7$ stands for an alkyl or aryl radical and $R_1$ has the same meaning as above, rearranging the resultant hydrazones of the formula

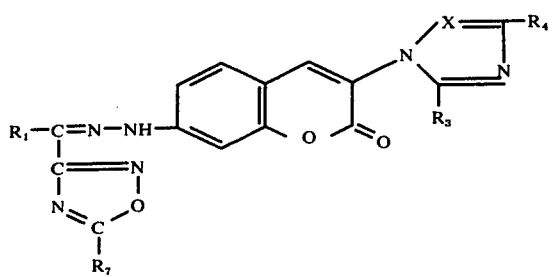

(XIa)

to form the 7-v-triazolyl-(2)-coumarin compounds of the formula

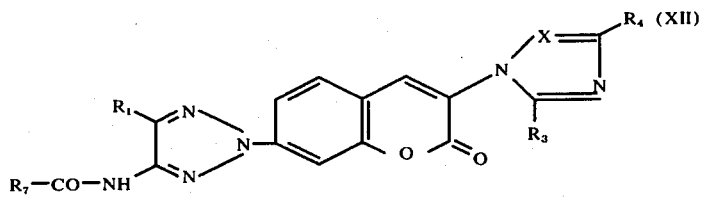

(XII)

and, if required, replacing the acylamino group $R_7$-CO-NH with the acylamino group $R_2$.

The rearrangement is preferably carried out by heating at temperatures of about 150° – 220° C.

The new triazolyl-coumarins of the formula (I) or (II) are valuable brightening agents. They are suitable for brightening fibres, filaments, fabrics, knitted fabrics, foils and plastic masses of synthetic origin, primarily for brightening materials of polyacrylonitrile, polyesters, polyamides, polyurethanes and cellulose esters.

Examples of compounds of the formula (I) which are suitable as brightening agents, are assembled in the following Table A. Examples of brightening agents of the formula (II) are assembled in Table B.

Table A

| $R_1$ | Brightening agents of the formula I $R_2$ | $R_3$ | $R_4$ | X |
|---|---|---|---|---|
| $CH_3$ | H | H | H | N |
| $CH_3$ | $CH_3$ | H | H | N |
| $CH_3$ | $CH_2$—$C_6H_5$ | H | H | N |
| $CH_3$ | $C_2H_5$ | H | H | N |
| $CH_3$ | n-$C_3H_7$ | H | H | N |
| i-$C_3H_7$ | $CH_3$ | H | H | N |
| n-$C_3H_7$ | $C_2H_5$ | H | H | N |
| $CH_3$ | $C_{10}H_{21}$ | H | H | N |
|  | —$(CH_2)_4$— | H | H | N |
| H | $C_6H_5$ | H | H | N |
| $C_6H_5$ | $CH_3$ | H | H | N |

Table A-continued

| | Brightening agents of the formula I | | | |
|---|---|---|---|---|
| $R_1$ | $R_2$ | $R_3$ | $R_4$ | X |
| $CH_3$ | CN | H | H | N |
| $CH_3$ | $CO_2C_2H_5$ | H | H | N |
| $C_6H_5$ | $CO_2C_2H_5$ | H | H | N |
| H | $CH_3CONH$ | H | H | N |
| H | $C_2H_5CONH$ | H | H | N |
| H | $(CH_3)_3CCONH$ | H | H | N |
| H | $C_2H_5OCONH$ | H | H | N |
| $CH_3$ | $CH_3$ | $CH_3$ | $CH_3$ | N |
| $C_2H_5$ | $CH_3$ | $CH_3$ | $CH_3$ | N |
| $CH_3$ | $CH_3$ | H | H | CH |
| $C_6H_5$ | H | H | H | CH |
| $C_6H_5$ | $C_6H_5$ | H | H | CH |
| $CH_3$ | $CH_3$ | H | $C_6H_5$ | N |
| $C_6H_5-CH_2-\phi-$ | $CH_3$ | H | H | N |
| $C_6H_5-CH_2O-\phi-$ | $CH_3$ | H | H | N |
| $-(CH_2)_4-$ | | H | H | N |
| o-tolyl-CH$_2-$ | | H | H | N |
| cyclohexyl- | phenyl- | H | H | N |
| biphenyl- | $CH_3$ | H | H | N |
| $C_6H_5-O-\phi-$ | $CH_3$ | H | H | N |

Table B

| | | | Brightening agents of the formula II | | | |
|---|---|---|---|---|---|---|
| $R_1$ | $R_2$ | $R_3$ | $R_4$ | X | $R_6$ | $Y^-$ |
| $CH_3$ | H | H | H | N | $CH_3$ | $CH_3O-SO_3^-$ |
| $CH_3$ | $CH_3$ | H | H | N | $CH_3$ | $CH_3O-SO_3^-$ |
| $CH_3$ | $CH_2-C_6H_5$ | H | H | N | $CH_3$ | $CH_3O-SO_3^-$ |
| $CH_3$ | $C_2H_5$ | H | H | N | $CH_3$ | $CH_3O-SO_3^-$ |
| $C_2H_5$ | $n-C_3H_7$ | H | H | N | $CH_3$ | $CH_3O-SO_3^-$ |
| H | $C_6H_5$ | H | H | N | $C_2H_5$ | $C_2H_5O-SO_3^-$ |
| $CH_3$ | $i-C_3H_7$ | H | H | N | $CH_3$ | $CH_3O-SO_3^-$ |

Table B-continued

| R₁ | R₂ | R₃ | R₄ | X | R₆ | Y⁻ |
|---|---|---|---|---|---|---|
| —(CH₂)₄— | | H | H | N | CH₃ | CH₃O—SO₃⁻ |
| CH₃ | H | H | H | N | C₄H₉ | Br⁻ |
| CH₃ | CH₃ | H | H | N | CH₂—C₆H₅ | Cl⁻ |
| CH₃ | CN | H | H | N | CH₃ | CH₃O—SO₃⁻ |
| H | C₂H₅CONH | H | H | N | CH₃ | CH₃O—SO₃⁻ |
| CH₃ | C₂H₅ | CH₃ | CH₃ | N | CH₃ | CH₃O—SO₃⁻ |
| CH₃ | CH₃ | H | H | CH | CH₃ | CH₃O—SO₃⁻ |
| C₂H₅ | C₃H₇ | H | H | CH | CH₃ | CH₃—C₆H₄—SO₃⁻ |
| C₆H₅ | H | H | H | CH | C₂H₅ | C₂H₅O—SO₃⁻ |
| CH₃ | CH₃ | H | C₆H₅ | N | CH₃ | CH₃O—SO₃⁻ |
| CH₃ | COOC₂H₅ | H | H | N | CH₃ | CH₃O—SO₃⁻ |

Preferred compounds are those of the formula

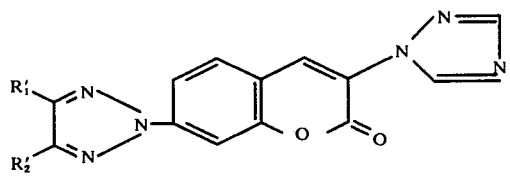

in which R₁' and R₂' stand for an alkyl radical with 1 – 4 carbon atoms, or in which R₁' stands for an optionally substituted phenyl radical and R₂' stand for hydrogen or an alkyl radical with 1 – 4 carbon atoms, and those of the formula

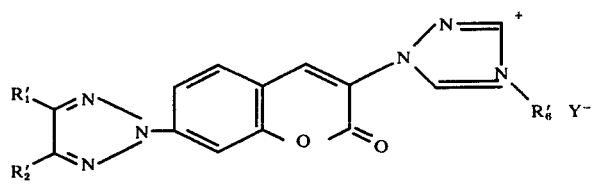

in which R₁' and R₂' have the same meaning as above; R₆' stands for an alkyl radical with 1 – 4 carbon atoms; and Y⁻ denotes an anion.

The brightening agents of the present invention can be applied in the usual manner, for example, in the form of solutions in water or organic solvents, or in the form of aqueous dispersions. Polyester materials can also be treated with the brightening agents by impregnating them with solutions or dispersions of the brightening agent, then squeezing, drying and briefly heating them at temperatures above 150° C. The brightening agents can also be added to casting or spinning masses serving for the production of synthetic fibres, filaments, foils and other products. The amounts required can easily be established in each case; in general, amounts of 0.05 to 0.6%, referred to the material to be brightened, have proved sufficient.

The brightening agents according to the invention give very good yields and are characterised by a high maximum degree of whiteness; the brightening effects (XIII)

achieved with them are very fast to light.

EXAMPLE 1

Preparation of 3-[1,2,4-triazolyl-(1)]-7-[4-methyl-5-ethyl-v-triazolyl-(2)]-coumarin (c)

(XIV)

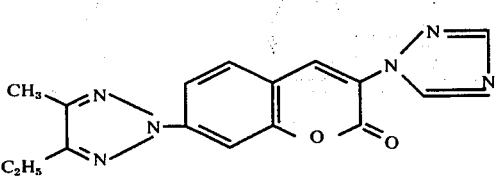

7-amino-3-[1,2,4-triazolyl-(1)]-coumarin:

A mixture of 254 g 4-acetylamino-salicylideneaniline, 163 g 1,2,4-triazolyl-(1)-acetic acid, 99 g of anhydrous sodium acetate and 510 g acetic anhydride is heated at a temperature of 145° C for 12 hours while stirring. The mixture is then allowed to cool to 100° C, mixed in the course of 30 minutes with 500 ml of concentrated hydrochloric acid, and the mixture is boiled under reflux for 4 hours. The content of the flask is subsequently poured into 5 litres of ice-water and adjusted to pH 1.5 by means of a concentrated sodium hydroxide solution. The precipitated product is filtered off with suction, the filter cake is suspended in 3 litres of water and the mixture is rendered ammoniacal. The product is again filtered off with suction, washed with water, and dried at 120° C. 148 g aminotriazolyl-coumarin of melting point 265° – 268° C are obtained.

7-hydrazino-3-[1,2,4-triazolyl-(1)]-coumarin:

148 g amino-triazolyl-coumarin are dissolved hot in a mixture of 750 ml of concentrated hydrochloric acid and 750 ml of water. The solution is cooled to 0° C and diazotised with a solution of 45 g sodium nitrite in 150 ml of water. Stirring is continued for 1 hour and the clear diazo solution is poured at 0° C into a mixture of 294 g tin(II) chloride and 600 ml of concentrated hydrochloric acid. The reaction mixture is stirred for another hour and then poured into 3 litres of water. The precipitated hydrazino-triazolyl-coumarin hydrochloride is filtered off with suction, suspended in 3 litres of warm water, and the mixture is rendered ammoniacal. The product is again filtered off with suction, the precipitate is washed with water and dried. 127 g 7-hydrazino-3-triazolyl-coumarin of melting point 249° C (decomp.) are thus obtained. 2-oximino-pentanone-(3)-N-[3-as-triazolyl-coumarinyl-(7)]-hydrazone: 127 g hydrazino-triazolyl-coumarin are stirred with 63 g 2-oximino-pentanone-(3) and 40 ml of 50% acetic acid in 500 ml glycol monomethyl ether at 98° – 100° C for 4 hours. 450 ml of the solvent are subsequently distilled off under reduced pressure and the residue is stirred with 1 litre of water for a short time. The precipitated yellow-brown crystalline oximino-hydrazone is then filtered off with suction, washed with water, and dried at 80° C under reduced pressure. 173 g oximino-hydrazone are obtained in the form of a brown-yellow crystal powder of melting point 275° – 276° C (decomp.).

3-[1,2,4-triazolyl-(1)]-7-[4-methyl-5-ethyl-v-triazolyl-(2)]-coumarin:

173 g of dry oximino-pentanone-triazolyl-coumarinylhydrazone are stirred with 61 g acetic anhydride and 16 g of anhydrous sodium acetate in 300 ml dimethyl formamide. The mixture is heated within one hour to 100° –105° C, this temperature is maintained for 3 hours and stirring is continued at 120° – 125° C for one hour. The mixture is subsequently evaporated to dryness on a water bath under reduced pressure. The residue is well stirred with 750 ml of water; the light-grey crystalline precipitate is filtered off with suction, washed with water and dried at 100° C. The crude product so obtained is recrystallised once from chlorobenzene and once from methyl glycol for purification. 128 g of the desired triazolyl-coumarin are obtained in the form of slightly greenish white crystals of melting point 224° – 225° C.

The 3-as-triazolyl-7-v-triazolyl-coumarins assembled in the following Table can be prepared in an analogous manner from 7-hydrazino-3-as-triazolyl-coumarin and the specified oximino-ketones.

Table

Brightening agents of the formula

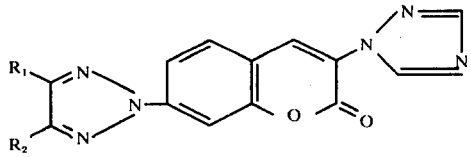

| Compound | R₁ | R₂ | Oximino-ketone |
|---|---|---|---|
| (a) | CH₃ | H | oximino-acetone |
| (b) | CH₃ | CH₃ | diacetyl monoxime |
| (c) | CH₃ | C₂H₅ | 2-oximino-pentanone-(3) |
| (d) | CH₂—C₆H₅ | CH₃ | 1-phenyl-2-oximino-butanone-(3) |
| (e) | iso-C₃H₇ | CH₃ | 3-oximino-4-methyl-pentanone-(2) |
| (f) | n-C₃H₇ | C₂H₅ | 3-oximino-heptanone-(4) |
| (g) | CH₃ | C₁₀H₂₁ | 3-oximino-tridecanone-(2) |
| (h) | —(CH₂)₄— | | 2-oximino-cyclohexanone-(1) |
| (i) | H | C₆H₅ | Oximino-acetophenone |
| (k) | C₆H₅ | CH₃ | 1-oximino-1-phenyl-acetone |
| (l) | C₆H₅ | C₆H₅ | benzil monoxime |
| (m) | C₆H₅—CH₂—⟨C₆H₄⟩— | CH₃ | p-benzyl-oximino-propiophenone |
| (m₁) | p-C₆H₄—C₆H₅ | CH₃ | p-phenyl-oximino-propiophenone |

Preparation of 3-[imidazolyl-(1)]-7-[4-methyl-5-ethyl-v-triazolyl-(2)]-coumarin (o):

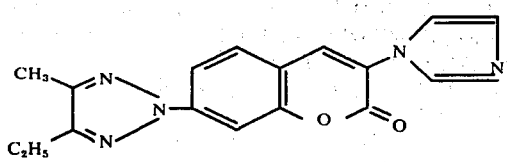

7-amino-3-[imidazolyl-(1)]-coumarin:

A mixture of 510 g acetic anhydride, 98 g of anhydrous sodium acetate and 151 g imidazolyl-(1)-acetic acid is stirred at 40° – 50° C for 1 hour, mixed with 254 g 4-acetylamino-salicylidene-aniline and stirred at 140° C for 20 hours. The temperature is then allowed to drop to 100° C, 570 g of concentrated hydrochloric acid are slowly added, and heating is continued under reflux for 4 hours. The reaction mixture is then turned out on to 2 kg of ice and adjusted to pH 3.8 by means of a concentrated sodium hydroxide solution. The precipitated dark product is filtered off with suction, washed with water, and dried at 110° C. In this way there are obtained 105 g of dry crude amino-imidazolyl-coumarin; after recrystallisation from o-dichlorobenzene and 80% dimethyl formamide, it is present in the form of pale yellow small crystals of melting point 272° – 275° C. 7-hydrazino-3-[imidazolyl-(1)]-coumarin:

45.4 g 7-amino-3-[imidazolyl-(1)]-coumarin are boiled in 200 ml of concentrated hydrochloric acid. After cooling to 0° C, the suspension of the colourless amine hydrochloride so obtained is diazotised, with a solution of 14 g sodium nitrite in 40 ml of water, while stirring. A solution of 92 g tin(II) chloride dihydrate in 200 ml of concentrated hydrochloric acid is slowly added dropwise at 0° C to the resultant clear diazo solution. Stirring is continued for 1 hour, the precipitated product is filtered off with suction, suspended in 1.2 litres of water, and the mixture is rendered alkaline with ammonia. The precipitated base is subsequently filtered off with suction, dried, and recrystallised from glycol monomethyl ether acetate. 39 g of the desired hydrazino-imidazolyl-coumarin are obtained in the form of yellow small crystals of melting point 256° C (decomp.). 2-oximino-pentanone-(3)-N-[3-imidazolyl-coumarinyl-(7)]-hydrazone:

24 g hydrazino-imidazolyl-coumarin and 13 g 2-oximino-pentanone-(3) are stirred with 5 ml glacial acetic acid in 120 ml glycol monomethyl ether at 98° – 100° C for 3½ hours. The bulk of the solvent is then distilled off under reduced pressure on a water bath and the residue is digested with 250 ml of water. The precipitated yellow-brown oximinohydrazone is filtered off with suction, washed with water, and dried at 80° C. 33.5 g of a yellow-brown crystal powder of melting point 270° – 274° C (decomp.) are obtained. 3-[imidazolyl-(1)]-7-[4-methyl-5-ethyl-v-triazolyl-(2)]-coumarin (o)

33.5 g of dry oximino-pentanone-imidazolyl-coumarinyl-hydrazone are stirred in 80 ml dimethyl formamide with 10.8 g acetic anhydride and 5 g sodium acetate at 50° – 60° C for 1 hour. The mixture is subsequently heated within 30 minutes to 110° C and heating is continued at 110° – 120° C for 2 hours. The reaction mixture is then evaporated to dryness under reduced pressure on a water bath and the residue is well stirred with 300 ml of water. The pale grey precipitate is filtered off with suction, thoroughly washed with water, dried and recrystallised for purification from chlorobenzene and subsequently from methyl glycol or dimethyl formamide. 19 g of the desired triazolyl-coumarin are obtained in the form of almost colourless slightly yellowish crystals.

In an analogous manner, the following 3-imidazolyl-7-v-triazolyl-coumarins are obtainable, for the preparation of which 7-v-hydrazino-3-imidazolyl-coumarin is condensed with the specified oximino-ketones.

Table

Brightening agents of the formula

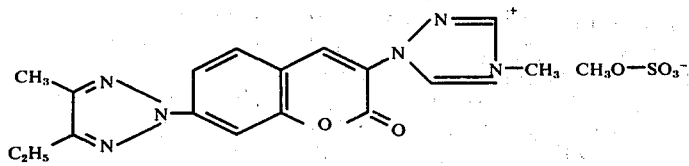

| Compound | R₁ | R₂ | Oximino ketone |
|---|---|---|---|
| (n) | CH₃ | CH₃ | diacetyl monoxime |
| (o) | CH₃ | C₂H₅ | 2-oximino-pentanone-(3) |
| (p) | C₂H₅ | n-C₃H₇ | 3-oximino-heptanone-(4) |
| (q) | iso-C₃H₇ | CH₃ | 3-oximino-4-methyl-pentanone-(2) |
| (r) | —(CH₂)₄— | | 2-oximino-cyclohexanone-(1) |
| (s) | C₆H₅ | H | oximino-acetophenone |
| (t) | CH₃ | C₆H₅ | oximino-propiophenone |

EXAMPLE 2

Preparation of 3-[4-methyl-1,2,4-triazolylium-(1)]-7-[4-methyl-5-ethyl-v-triazolyl-(2)]-coumarin methosulphate (o)

161 g 3-[1,2,4-triazolyl-(1)]-7-[4-methyl-5-ethyl-v-triazolyl-(2)]-coumarin (Example 1c) are dissolved hot in 800 ml chlorobenzene while stirring. 69 g of distilled dimethyl sulphate are added dropwise at 130° C within about 20 minutes. The mixture is stirred for a further hour at 130° C; during this time the triazolium salt formed is precipitated almost quantitatively in the form of long light-coloured, slightly yellowish needles. The mixture is subsequently allowed to cool to 50° – 60° C, the precipitated crystals are filtered off with suction, washed with chlorobenzene, and dried at 80° – 100° C. 222 g 3-[4-methyl-1,2,4-triazolylium-(1)]-7-[4-methyl-5-ethyl-v-triazolyl-(2)]-coumarin methosulphate are obtained in the form of almost colourless crystals which decompose at 234° – 236° C and readily dissolve in water.

The following triazolium and imidazolium salts are obtained in an analogous manner from the 3-[as-triazolyl- or imidazolyl]-7-v-triazolyl-coumarins mentioned in Example 1 under (a) to (t) and the specified quaternising agents.

about 80° C, the precipitated light-coloured triazolium methosulphate is filtered off with suction, washed with chlorobezene, and dried. It is obtained in the form of light-coloured yellowish crystals which decompose at 225° – 235° C and readily dissolve in water.

Table

Brightening agents of the formula

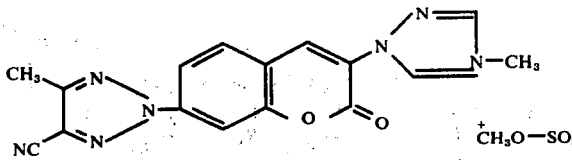

| Compound | $R_1$ | $R_2$ | $R_6$ | X | Y | Quaternising agent |
|---|---|---|---|---|---|---|
| (a) | $CH_3$ | H | $CH_3$ | N | $CH_3SO_4^-$ | dimethyl sulphate |
| (b) | $CH_3$ | $CH_3$ | $CH_3$ | N | $CH_3SO_4^-$ | dimethyl sulphate |
| (c) | $CH_3$ | $C_2H_5$ | $CH_3$ | N | $CH_3SO_4^-$ | dimethyl sulphate |
| (d) | $CH_2-C_6H_5$ | $CH_3$ | $CH_3$ | N | $CH_3SO_4^-$ | dimethyl sulphate |
| (e) | $i-C_3H_7$ | $CH_3$ | $CH_3$ | N | $CH_3SO_4^-$ | dimethyl sulphate |
| (f) | $C_2H_5$ | $n-C_3H_7$ | $CH_3$ | N | $CH_3SO_4^-$ | dimethyl sulphate |
| (g) | $CH_3$ | $C_{10}H_{21}$ | $CH_3$ | N | $CH_3SO_4^-$ | dimethyl sulphate |
| (h) | $-(CH_2)_4-$ | | $C_2H_5$ | N | $C_2H_5SO_4^-$ | dimethyl sulphate |
| (i) | H | $C_6H_5$ | $CH_3$ | N | $CH_3SO_4^-$ | dimethyl sulphate |
| (k) | $C_6H_5$ | $CH_3$ | $CH_2C_6H_5$ | N | $Cl^-$ | benzyl chloride |
| (l) | $C_6H_5$ | $C_6H_5$ | $CH_3$ | N | $CH_3-C_6H_4-SO_3^-$ | p-toluene-sulphonic acid methyl ester |
| (m) | $CH_3$ | $CH_3$ | $C_2H_5$ | CH | $C_2H_5SO_4^-$ | diethyl sulphate |
| (n) | $CH_3$ | $C_2H_5$ | $CH_3$ | CH | $CH_3SO_4^-$ | dimethyl sulphate |
| (o) | $C_2H_5$ | $n-C_3H_7$ | $CH_3$ | CH | $CH_3SO_4^-$ | dimethyl sulphate |
| (p) | $i-C_3H_7$ | $CH_3$ | $C_3H_5$ | CH | $Br^-$ | allyl bromide |
| (q) | $-(CH_2)_4-$ | | $CH_3$ | CH | $CH_3SO_4^-$ | dimethyl sulphate |
| (r) | $C_6H_5$ | H | $CH_3$ | CH | $CH_3SO_4^-$ | dimethyl sulphate |
| (s) | $CH_3$ | $C_6H_5$ | $CH_3$ | CH | $CH_3SO_4^-$ | dimethyl sulphate |

EXAMPLE 3

Preparation of 3-[1,2,4-triazolylium-(1)]-7-[4-methyl-5-cyano-v-triazolyl-(2)]-coumarin methosulphate.

23 g 7-amino-3-triazolyl-coumarin are stirred with 60 ml of concentrated hydrochloric acid and 60 ml of water while heating. The light-coloured solution is cooled to +5° C and diazotised by slowly adding a solution of 7 g sodium nitrite in 30 ml of water, a clear solution being formed. The excess hydrochloric acid is subsequently buffered by the addition of sodium carbonate, and the diazo suspension is poured into a solution of 9 g β-amino-crotonitrile (diacetonitrile) in 300 ml of alcohol, while maintaining a pH value of 5 – 6. When the coupling is completed, a dilute sodium chloride solution is added to the mixture, the precipitated brown-yellow azo compound is filtered off with suction and dissolved in 200 ml pyridine. 45 g copper acetate are gradually added with stirring and the mixture is heated to 75° – 80° C. As soon as the cyclisation reaction is completed (about 3 hours), the pyridine is driven off with steam and the residue purified by reprecipitation from chlorobenzene and dimethyl formamide. 10 g of the light-coloured 3-as-triazolyl-7-[4-methyl-5-cyano-v-triazolyl-(2)]-coumarin so obtained are dissolved in 75 ml chlorobenzene and the solution is stirred with 5 g dimethyl sulphate at 130° C for 2 hours. The mixture is subsequently allowed to cool to If β-aminocrotonic acid ethyl ester is used as coupling component, instead of β-aminocrotonitrile, and the process is carried out in an analogous manner, then there is obtained 3-[1,2,4-triazolylium-(1)]-7-[4-methyl-5-carboethoxy-v-triazolyl-(2)]-coumarin methosulphate which also dissolves readily in water and the solutions of which are strongly fluorescent.

EXAMPLE 4

Polyacrylonitrile fibres are introduced in a liquor ratio of 1 : 40 into an aqueous bath containing, per litre, 1 g oxalic acid, 1 g sodium chlorite and 0.05 g of one of the compounds mentioned in Example 2 under (a) to (f), (h), (i) and (m) to (r) or in Example 3. The bath is heated to boiling temperature within 20 minutes and kept at this temperature for 45 – 60 minutes. The polyacrylonitrile fibres are subsequently rinsed and dried. The fibres are then excellently brightened.

EXAMPLE 5

One of the compounds mentioned in Example 2 under (a) to (i) is added to a conventional polyacrylonitrile spinning solution in such an amount that the concentration of this compound in the extruded polyacrylonitrile fibre amounts to 0.1 per cent by weight. The spinning solution is extruded in the usual manner and the material produced is moved about for 45 minutes in a liquor ratio of 1 : 40 in an aqueous bath at 95° C containing, per litre, 1 g sodium chlorite and 1 g oxalic acid. The fibres obtained are then pure white.

EXAMPLE 6

Fibres of polyethylene glycol terephthalate are introduced in a liquor ratio of 1 : 40 into a bath containing, per litre, 1 g oleyl sulphate, 0.75 g formic acid and 0.1 g of one of the compounds mentioned in Example 1 under (c), (d), (e), (f), (m), (n), (o) and (p). The bath is subsequently heated to boiling temperature and kept at this temperature for 30 – 60 minutes. After rinsing and drying, the polyester fibres exhibit a very good brightening effect.

EXAMPLE 7

A fabric of polyester fibre is padded with an aqueous liquor containing, per litre, 1 g of a commercial dispersing agent based on fatty alcohol polyglycol ethers, 1 g of a commercial wetting agent based on alkylnaphthalene-sulphonic acids, 4 g of an alginate thickening agent and a solution of 1 g of one of the compounds mentioned in Example 1 under (a) to (t) in 20 g triethanolamine. The fabric is then squeezed to a weight increase of 100%, then dried, heated at 190° C for 1 minute, and subsequently washed hot. Compared with untreated fabric, the material exhibits a very strong and clear brightening effect of excellent fastness to light, washing and chlorite.

EXAMPLE 8

A fabric of cellulose acetate fibres is introduced in a liquor ratio of 1 : 40 into a bath containing, per litre, 1 g oleyl sulphonate, 0.75 g formic acid and 0.08 g of one of the brightening agents mentioned in Example 1 under (c) to (f) (m) and (o) to (q). The bath is then heated to 60° C within 20 minutes and kept at this temperature for 30 – 60 minutes. After rinsing and drying, the fabric exhibits a brilliant brightening effect.

We claim:

1. A triazolyl coumarin of the formula

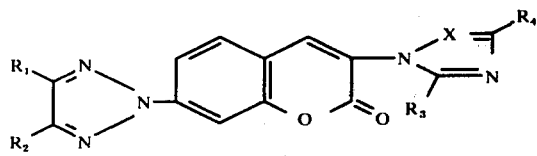

wherein
$R_1$ is
 a. hydrogen;
 b. $C_{1-12}$-alkyl which may be substituted by halogen, hydroxy, $C_{1-4}$ alkoxy, $C_{1-4}$ alkyl carbonyl, COOH, $C_{1-4}$ alkoxycarbonyloxy, phenyl, halo-phenyl, lower alkyl phenyl, or lower alkoxy phenyl;
 c. cyclohexyl; or
 d. phenyl which may be substituted by fluoro, chloro, bromo, CN, $C_{1-4}$-alkyl, $C_{1-4}$-alkoxy, phenyl $C_{1-4}$-alkyl, carboxy $C_{1-4}$-alkyl, phenyl $C_{1-4}$-alkoxy, carboxy $C_{1-4}$-alkoxy, $C_{1-5}$-alkoxy carbonyl, $C_{1-4}$-alkyl sulfonyl, phenyl or phenoxy;
$R_2$ is H or is
 a. $R_1$;
 b. CN;
 c. COOH;
 d. $C_{1-4}$-alkoxy carbonyl;
 e. $CONH_2$;
 f. N-$C_{1-4}$-alkyl carbonamide;
 g. N,N-di-$C_{1-4}$-alkyl carbonamide;
 h. or acylamino wherein acyl is selected from the class consisting of alkoxycarbonyl with 1–4 carbon atoms in the alkoxy group; alkyl carbonyl with 1–10 carbon atoms in the alkyl radical; phenyl carbonyl; or substituted acyl as defined above but additionally containing a substituent selected from the class consisting of halogen, amino, phenyl, ethoxy, methoxy, propoxy, methyl, dimethylamino, diethylamino, or dipropylamino;

$R_1$ and $R_2$ together with the two carbon atoms of the triazole ring may form a member selected from the group consisting of

and 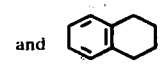

and
$R_3$ and $R_4$, independently of one another are selected from the group consisting of hydrogen, alkyl with 1–4 carbon atoms and phenyl;
X is N or C-$R_5$ where $R_5$ is H or alkyl with 1–4 carbon atoms or their quaternization products of the formula

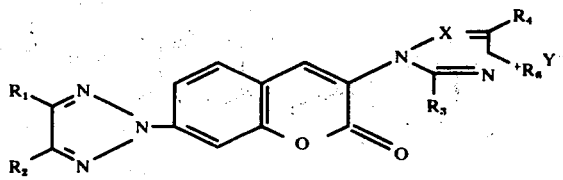

where $Y^-$ is an anion, and
$R_6$ is selected from the group consisting of alkyl with 1–12 carbon atoms, which is unsubstituted or substituted by a member of the class consisting of halogen; OH; alkoxy with 1–4 carbon atoms; alkyl carbonyloxy with 1–4 carbon atoms in the alkyl radical; COOH; alkoxy carbonyl with 1–4 carbon atoms in the alkyl group; phenyl; halophenyl; lower alkyl phenyl, and alkoxy-phenyl.

2. Triazolyl-coumarins of the formula

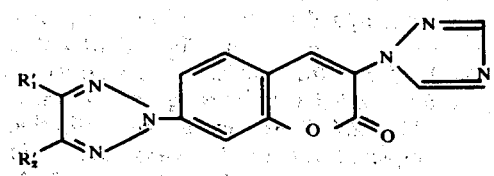

in which $R_1'$ and $R_2'$ stand for an alkyl radical with 1 – 4 carbon atoms, or in which $R_1'$ stands for phenyl and $R_2'$ stands for hydrogen or an alkyl radical with 1 – 4 carbon atoms, and their quaternisation products of the formula

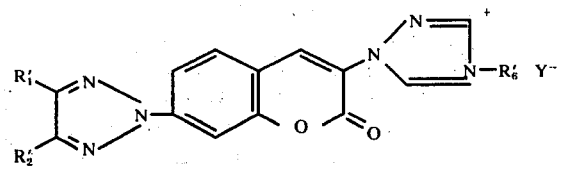

in which $R_1'$ and $R_2'$ stand for an alkyl radical with 1–4 carbon atoms; $R_6'$ stands for an alkyl radical with 1–4 carbon atoms; and $Y^-$ means an anion.

3. The triazolyl-coumarin of the formula:

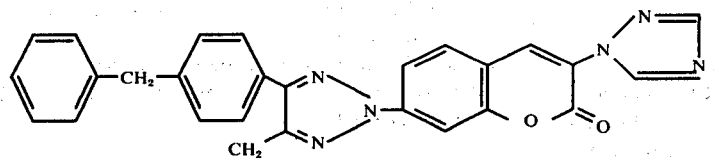

4. The triazolyl-coumarin of the formula:

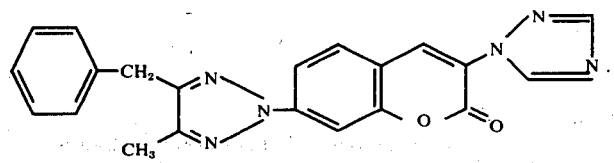

5. The triazolyl-coumarin of the formula:

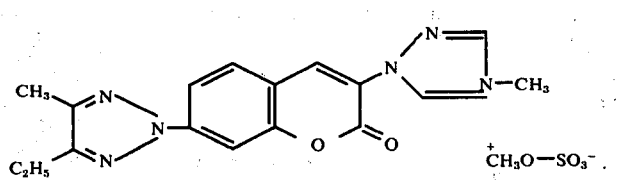

$\overset{+}{C}H_3O-SO_3^-$.

6. The triazolyl-coumarin of the formula:

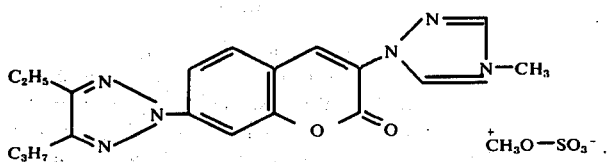

$\overset{+}{C}H_3O-SO_3^-$.

7. The triazolyl-coumarin of the formula:

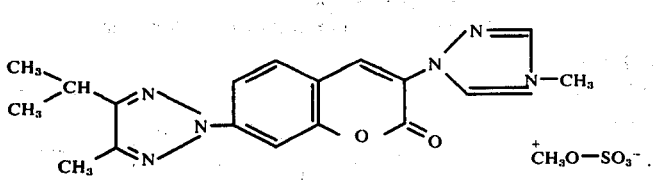

$\overset{+}{C}H_3O-SO_3^-$.

8. A compound of claim 1 wherein $R_1$ and $R_2$ are selected from the group consisting of hydrogen, alkyl with 1–4 carbon atoms, benzyl, phenyl, chlorophenyl, fluorophenyl, bromophenyl, methylphenyl, methoxyphenyl, ethylphenyl, butylphenyl, phenylphenyl, benzylphenyl, benzyloxy or wherein $R_1$ and $R_2$ together form a cyclohexyl or cyclopentyl radical and wherein Y is a colorless anion.

* * * * *